United States Patent [19]
Phillips

[11] Patent Number: 5,465,728
[45] Date of Patent: Nov. 14, 1995

[54] BREATH COLLECTION

[76] Inventor: Michael Phillips, 156 Center Ave., Chatham, N.J. 07928

[21] Appl. No.: 179,918

[22] Filed: Jan. 11, 1994

[51] Int. Cl.$^6$ .................................................. A61B 5/097
[52] U.S. Cl. ........................................ 128/730; 128/204.17
[58] Field of Search ............................... 128/719, 730, 128/204.17, 205.27, 718, 716; 73/23.3; 422/84

[56] References Cited

U.S. PATENT DOCUMENTS

| | | | |
|---|---|---|---|
| 3,858,573 | 1/1975 | Ryan et al. | 128/730 |
| 4,221,224 | 9/1980 | Clark | 128/718 |
| 4,671,298 | 8/1987 | Babb et al. | 128/719 |
| 4,852,583 | 8/1989 | Walker | 128/719 |
| 5,042,501 | 8/1991 | Kenny et al. | 128/719 |

*Primary Examiner*—William E. Kamm
*Assistant Examiner*—Brian M. Green
*Attorney, Agent, or Firm*—Kane, Dalsimer, Sullivan, Kurucz, Levy, Eisele and Richard

[57] ABSTRACT

Apparatus which is highly portable and even hand-held is used to collect mammalian breath for chemical analysis and as a diagnostic tool for the physician. The apparatus comprises a fluid reservoir container having first and second ends and a body extending between these ends so as to define an interior chamber; a breath entry portal; a breath exit portal; a sampling portal; a jacket to maintain the temperature of the chamber; a sample container for holding samples of exhaled breath; and pump means for moving selected samples of breath from the reservoir container into the sample container.

12 Claims, 5 Drawing Sheets

BREATH COLLECTION

BACKGROUND OF THE INVENTION

1. Field of the Invention

The invention relates to diagnostic medical instruments and more particularly to apparatus for the collection and analysis of alveolar breath.

2. Brief Description of Related Art

Normal mammalian breath, including human alveolar breath contains a large number of volatile organic compounds in low concentrations (nanomolar or picomolar). Many of these compounds originate from the capillary blood; they enter the alveoli of the lungs by diffusion across the pulmonary alveolar membrane. Therefore, the analysis of breath opens a unique window onto the composition of the blood.

The collection and analysis of the breath presents several technical difficulties, but may yield information of considerable medical interest. There is evidence that the composition of alveolar breath may be altered in several disorders, including lung cancer, liver disease, inflammatory bowel disease, rheumatoid arthritis and schizophrenia. The chemical analysis of breath therefore provides a non-invasive diagnostic test for the diagnosis of these and other diseases.

The major technical difficulties in chemical analysis of breath arise from:

(1) the large numbers of volatile organic compounds (possibly 100 or more) found in breath and necessitating separation prior to assay (e.g.; by gas chromatography combined with mass spectroscopy) (GC/MS), and (2) the very low concentration of the compounds, which are below the limits of sensitivity of currently available GC/MS instruments, therefore necessitating concentration of the breath prior to analysis.

The above-described difficulties may be circumvented by the use of a breath collecting apparatus which collects and concentrates the breath into a sample suitable for assay by GC/MS. However, the design and operation of an effective breath collecting apparatus presents a number of technical requirements:

(1) Subject comfort: the apparatus should present no significant resistance to exhalation (which might cause discomfort for the subject providing a breath sample).

(2) Subject safety: the apparatus should provide no hazard to the subject, such as exposure to potential sources of inhaled infectious microorganisms.

(3) Freedom from contamination: the apparatus should not incorporate any structural components such as plastics and adhesives containing volatile organic compounds which continuously outgas, causing contamination of the sample.

(4) Alveolar sampling: normal mammalian breath contains two components: the "dead space" breath originating from the pharynx, trachea and bronchial tree where no gaseous interchange occurs, and alveolar breath from the alveoli of the lungs which contains the volatile organic compounds of interest which have diffused from the blood. The sample should be drawn principally from alveolar breath, not dead space breath.

(5) Control of water condensation: Breath is saturated with water which condenses immediately onto cool surfaces in the breath collecting apparatus. This may result in partitioning of volatile organic compounds in the gaseous phase into the aqueous phase, with a consequent depletion of volatile organic compounds in the analyzed specimen.

(6) Concentration of sample: The ultimate purpose of the apparatus is to concentrate volatile organic compounds in the alveolar breath, while allowing the nitrogen, oxygen, and carbon dioxide in the breath to escape unhindered. The commonest concentration techniques are cryogenic (i.e.; capture in a cold trap), adsorptive (i.e.; capture in a trap containing an adsorptive resin or some other binding agent) or chemical (i.e.; capture by interaction with a chemical compound).

Early apparatus for the collection and analysis of alveolar breath was described by us in an article published in Clin. Chem., 38/1, 60–65 (1992). The state of the art was also described by us in Scientific American, Vol. 267, No. 1, July 1992, pps. 74–79. Although the apparatus of the present invention is superficially similar to the apparatus previously described by us, it contains a number of improvements which have resulted in functional advantages not previously enjoyed. For example, embodiment apparatus of the present invention:

(1) is transportable and operated by a technician or in portable embodiments of more complexity incorporates an arm containing the reservoir tube and the sampling tube; this arm can be swivelled at the end where it joins the device, in order to adjust to the height of the subject who is either seated or standing. The far end of this arm can be swivelled to accommodate the subject's mouth at a comfortable angle.

(2) Incorporates a heating system, in both the arm and the central structure. The sampling tube and the reservoir tube are heated throughout their length, in order to prevent condensation of water and volatile organic compounds.

(3) Eliminates the earlier need for supplying chemically purified air. Recent studies (unpublished) have shown that this procedure actually introduces impurities into the system, and yields inconsistent results with human subjects. With the subject breathing room air the results are more consistent and more easily interpreted than when chemically purified air is inspired.

(4) Eliminates the provision for drawing the sample through a water trap. This procedure entails the risk of contamination of the specimen, as well as the possibility of losing water soluble volatile organic compounds from the breath sample. The heating system renders a water trap unnecessary, thereby resulting in a simpler, chemically cleaner, and more dependable apparatus.

(5) Optionally eliminates provisions for a respirometer at the end of the reservoir tube. In practice, this was not found to be necessary.

(6) Optionally eliminates a number of heavy and bulky components, to be smaller and portable. It can be manufactured as a hand-carried device which no longer needs to be wheeled about on a cart or can even be miniaturized to be hand supported in use.

(7) May include provisions for alternative methods of collection of breath samples besides adsorptive trapping: i.e., cryogenic trapping, chemical trapping, evacuated container collections, and bag collections. It is considerably more versatile apparatus.

SUMMARY OF THE INVENTION

The invention comprises apparatus for the collection of alveolar breath from a mammal for analysis, which comprises;

A. a fluid reservoir container having
  (a) a first end;
  (b) a second end;
  (c) a container body extending from the first end to the second end, and which with the first and second ends defines an interior chamber, said body being of a configuration whereby breath introduced into the first end will travel to the second end when the second end is vented;
  (d) a breath entry portal in the body, proximal to the first end and distal to the second end;
  (e) a breath exit portal in the body, proximal to the second end and distal to the first end; and
  (f) a sampling portal in the body of the reservoir container, at a point between the entry and the exit portals;
B. valve means on the exit portal for controlled sealing and opening of the exit portal;
C. means for maintaining said chamber at a temperature sufficient to prevent condensation of water and volatile compounds in the mammal's breath, associated with the reservoir container;
D. means for sealed coupling of the reservoir container entry portal to the pulmonary airway of the mammal, whereby exhaled breath is directly delivered at full, undiluted concentration of compounds contained in the breath, to the reservoir container;
E. a sample container for holding samples of the breath exhaled by the mammal into the reservoir container and selected for analysis to determine quantitative presence of those compounds of interest;
F. valve means between the sampling portal of the reservoir container and the sample container for selectively directing breath samples from the reservoir container to the sample container;
G. means for maintaining the selected breath at a temperature sufficient to prevent water condensation in the sample contained and the valve means for directing samples to the sample containers; and
H. pump means for moving selected samples of the breath from the reservoir's container into the sample container.

The invention also comprises a method of obtaining undiluted, uncontaminated samples of alveolar breath from a mammal for analysis to determine the quantitative presence of volatile organic compounds of interest for determination.

DETAILED DESCRIPTION OF THE PREFERRED EMBODIMENTS OF THE INVENTION

Those skilled in the art will gain an appreciation of the invention from a reading of the following description of preferred embodiments of the invention in conjunction with a viewing of the accompanying drawings of FIGS. 1–4, inclusive.

Figure 1:
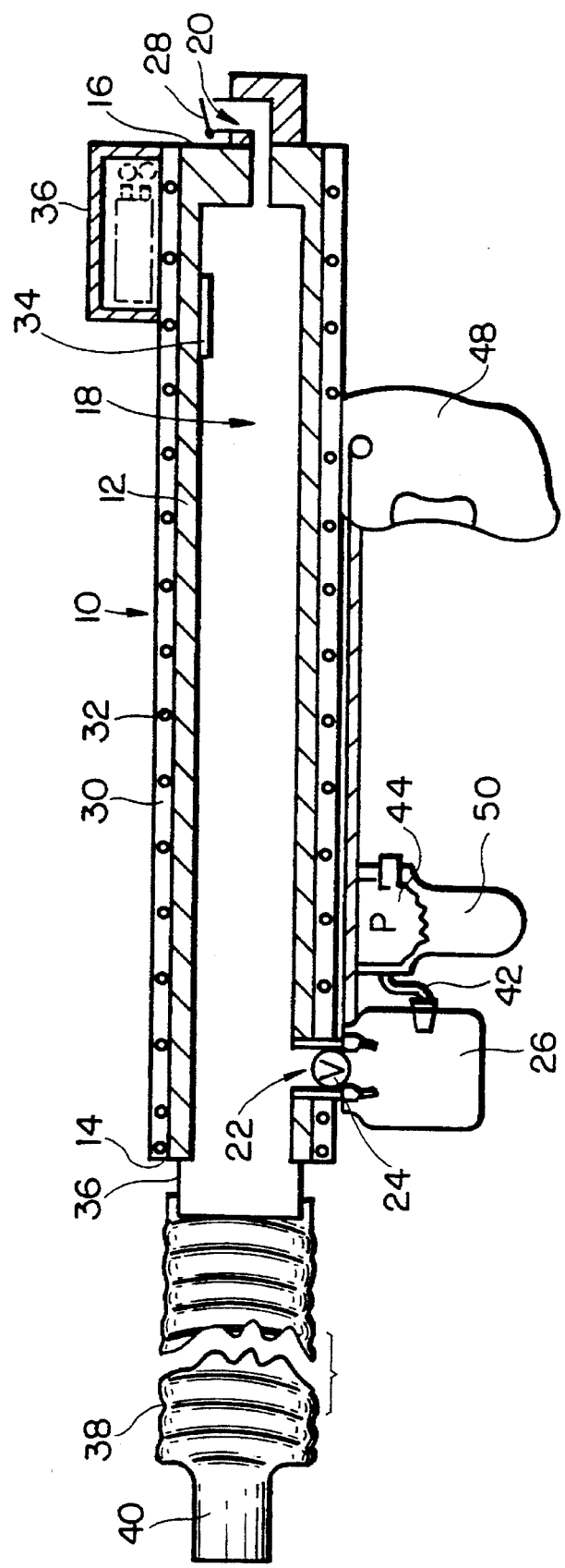
FIG. 1 is a cross-sectional view (in-part) of an embodiment apparatus of the invention.

FIG. 1 is a cross-sectional (in-part) side view of an embodiment apparatus 10 of the invention, adapted to be hand-held and operated by an operator-technician to collect human breath for chemical analysis. The apparatus 10 includes a tubular fluid (gas) reservoir container 12 having a first end 14 and a second end 16. The tubular container 12 body extends between the ends 14, 16 and with the ends 14, 16 defines an open interior chamber 18. The end 14 of the container 12 is open for access to the chamber 18 and functions as a breath entry portal, but end 16 is essentially closed, vented by a breath exit portal 20. A sampling portal 22 pierces the container 12 body at a point proximal to the end 14 and provides fluid communication between chamber 18 and the exterior of container 12. A valve 24 controls the communication so that samples of gas within the chamber 18 may be withdrawn from the chamber 18 or selected for collection in the vessel 26 mounted on the sampling portal 22, as will be described hereinafter. A spring action flap valve 28 is mounted on the outlet of vent 20 with sufficient spring force to maintain the vent 20 closed except when the subject is exhaling into the chamber 18. The body of container 12 is jacketed with a radiant energy heat sleeve 30 carrying a helical coil of electrical resistance wire 32 for the purpose of maintaining a pre-determined temperature (circa 40° C.) within the chamber 18. Advantageously, the outer surface of the sleeve 30 is thermally insulated so that the heat energy generated by the sleeve 30 is directed into the chamber 18. A thin-film thermistor 34 is mounted on the inner surface of chamber 18 and electrically connected to a rechargeable battery pack 36 as a means for sensing the temperature within chamber 18 and in response to predetermined temperature limits, energizing or de-energizing the sleeve 30 to maintain the predetermined temperature within the chamber 18. The end 14 of apparatus 10 carries a coupler 36 for sealed coupling with a breathing tube 38 (shown fragmented) adapted to collect breath from the pulmonary airway of a subject. For example, as shown in FIG. 1 a mouthpiece 40 may be an integrally molded part of tube 38, for insertion in the mouth of a human patient, sealed by the lips. Alternatively, and as examples, the mouthpiece can be replaced with means for coupling to a tracheostomy tube, a nasal piece or the like so that exhaled breath is directly delivered at full, undiluted concentration (of contained volatile organic compounds).

Vessel 26 is a sampling container for receiving selected sample of the breath delivered to chamber 18 from the subject. Advantageously, these samples are collected from the chamber 18 at a point close (proximal) to the end 14 and remote from end 16 of the container 12. The vessel 26 is hermetically sealed with portal 22 and connected by vacuum line 42 to an evacuation pump 44. The pump 44 may be mechanical or electrical in operation. For example, pump 44 may be a syringe pump for manual operation or a simple electrically powered membrane pump, connected electrically to the power pack 36 through switch means (not shown in FIG. 1). The vessel 26 may be any commercially available vacuum bottle or vessel which can be mounted to the outlet of portal 22. For example, an insulated Thermos ® type bottle or a Summa ® canister can be provided to maintain the pre-determined temperature of breath samples collected in the vessel 26 (not shown in FIG. 1). The valve 24 controls the opening and closing of portal 22 for selected sampling of the air collected in chamber 18, proximal to end 14. The valve 24 may be manually operable or operable by solenoid means. For purposes of clarity, the electrical wiring scheme for electrical control and operation of apparatus 10, re: switches, wires and controls have not been shown in FIG. 1. However, such devices are conventional and those skilled in the art will appreciate how to connect them for operation of sleeve 30, thermistor 34, valve 24, and pump 44. In the hand-held embodiment apparatus 10 the electrical controls such as switches are advantageously positioned and mounted on hand grip 48 for finger actuation. The fore-grip 50 enables the operator to readily support the apparatus 10 during operation.

Figure 2:
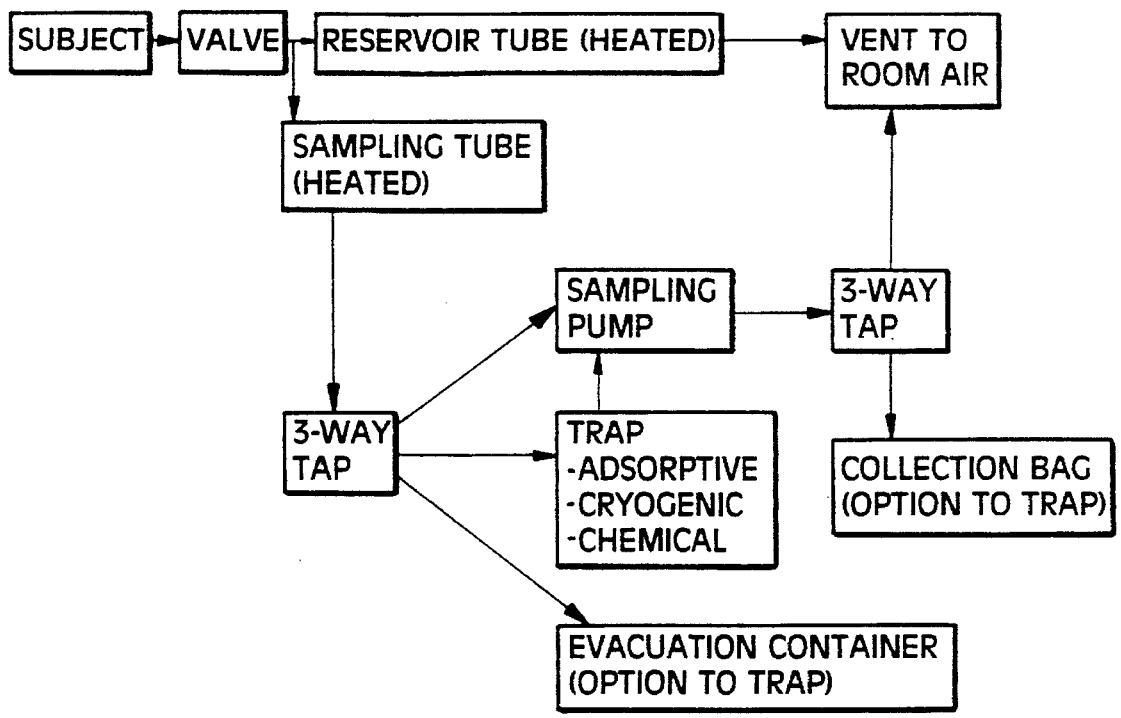
FIG. 2 is a schematic block diagram of an assembly, showing the components of an embodiment apparatus of the invention and their functional relationship, wherein the collected sample of breath is processed preparatory to chemical analysis.

The operation of the apparatus 10 is shown diagrammatically in FIG. 2. The apparatus fulfills the previously described technical requirements in the following fashion:

(1) Subject comfort: the subject blows into a wide-bore tube 38 (approx. 1 inch diameter) which provides very little resistance to expiration.

(2) Subject safety: Sterile disposable components (mouthpiece 40 and tube 38) are replaceable for each user.

(3) Freedom from chemical contamination: the apparatus may be constructed from components such as glass, stainless steel, and low-contamination plastics (e.g. Teflon ®) which do not out-gas volatile organic compounds to the sample.

(4) Alveolar sampling: the breath enters into a long wide-bore, chamber 18, which acts as a reservoir with a capacity of approximately 3 liters. With each expiration a column of breath enters into this reservoir with the deadspace breath furthest downstream at end 16. The sample removed for concentration is drawn from the reservoir at sampling port 22 close to the subject's mouth, i.e., from the upstream component which contains alveolar breath from deep in the lungs. The sample may be withdrawn at a rate which ensures that the alveolar breath in the reservoir is not depleted before the next expiration is delivered. Dead space breath passes the sampling port 22 for only a fraction of a second during each expiration, so that the selected and withdrawn sample is composed entirely of alveolar breath.

(5) Control of water condensation: The reservoir is heated to circa 40 deg C., in order to prevent any condensation of water or organic compounds within the system.

(6) Collection of sample: The warm alveolar breath may be drawn from the sampling port 22 through a heated tube, in order to prevent water or organic compound condensation. The sample of breath may then be processed in a number of different ways, according to the requirements of the user (as will be discussed further hereinafter).

FIG. 2 is a schematic block diagram of an assembly, showing the components of an apparatus of the invention and their functional relationship wherein the collected sample of breath is processed preparatory to chemical analysis. Thus, the sample of breath in the sampling vessel may be processed in a number of ways. For example, the heated sample by means of a 3-way tap can be directed to an adsorptive, cryogenic or chemical trap.

Adsorbent trapping: The alveolar breath is drawn through a trap containing an adsorbent agent or mixture of adsorbent agents which bind the volatile organic compounds in the sample while allowing the nitrogen and oxygen to pass through unhindered. The adsorbent trap may incorporate a number of agents, such as adsorptive resins (e.g. Tenax® or Carbotrap®) or activated carbon.

Cryogenic trapping: The alveolar breath may be drawn through a cold trap (e.g. a U-tube filled with glass beads, and immersed in liquid nitrogen), so that all volatile components are captured by freezing.

Chemical trapping: The alveolar breath may be drawn through a trap containing a chemical agent which binds one or more specific components of the alveolar breath by chemical interaction (e.g. Hyamine® a mixture of quaternary ammonium salts may be used to capture carbon dioxide). This procedure may be of special use in the measurement of radiolabelled compounds excreted in the breath.

Alternatively, as shown in FIG. 2, collected breath may be evacuated pumped into a bag, for subsequent assay and/or concentration in the laboratory.

Figure 3:
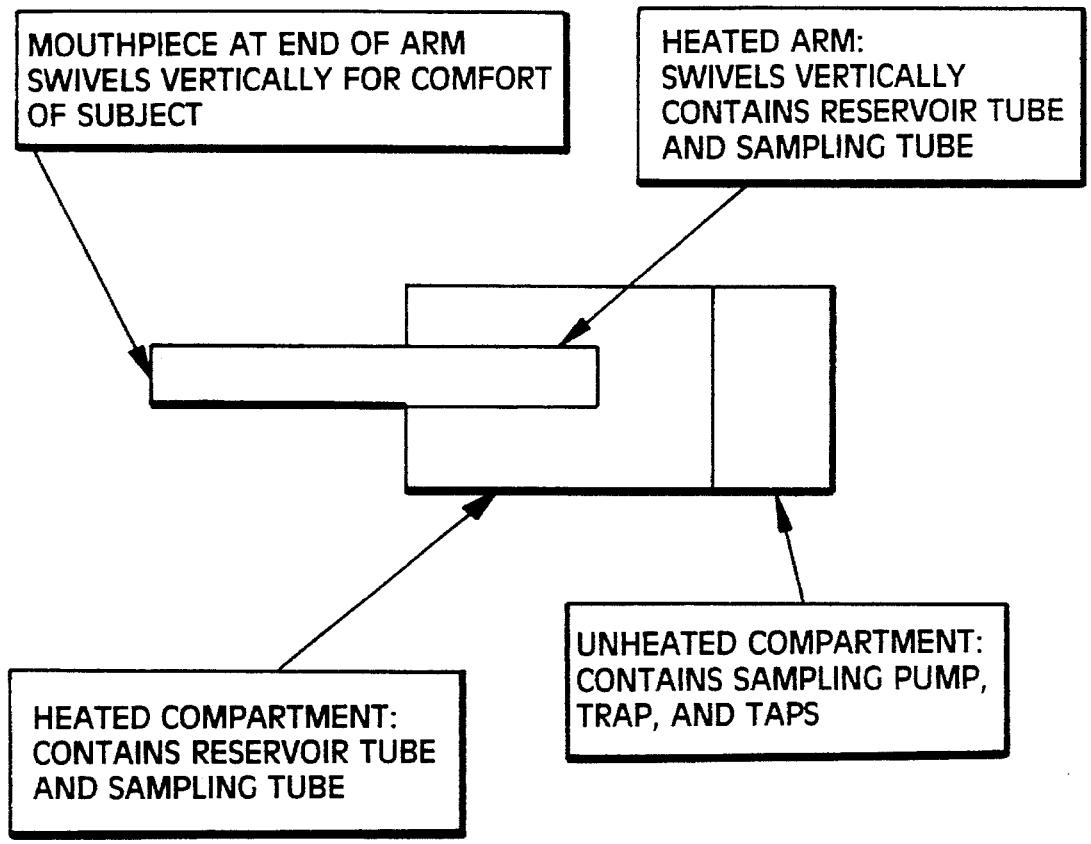
FIG. 3 is a schematic block diagram showing partially a preferred embodiment apparatus of the invention.
Figure 4:
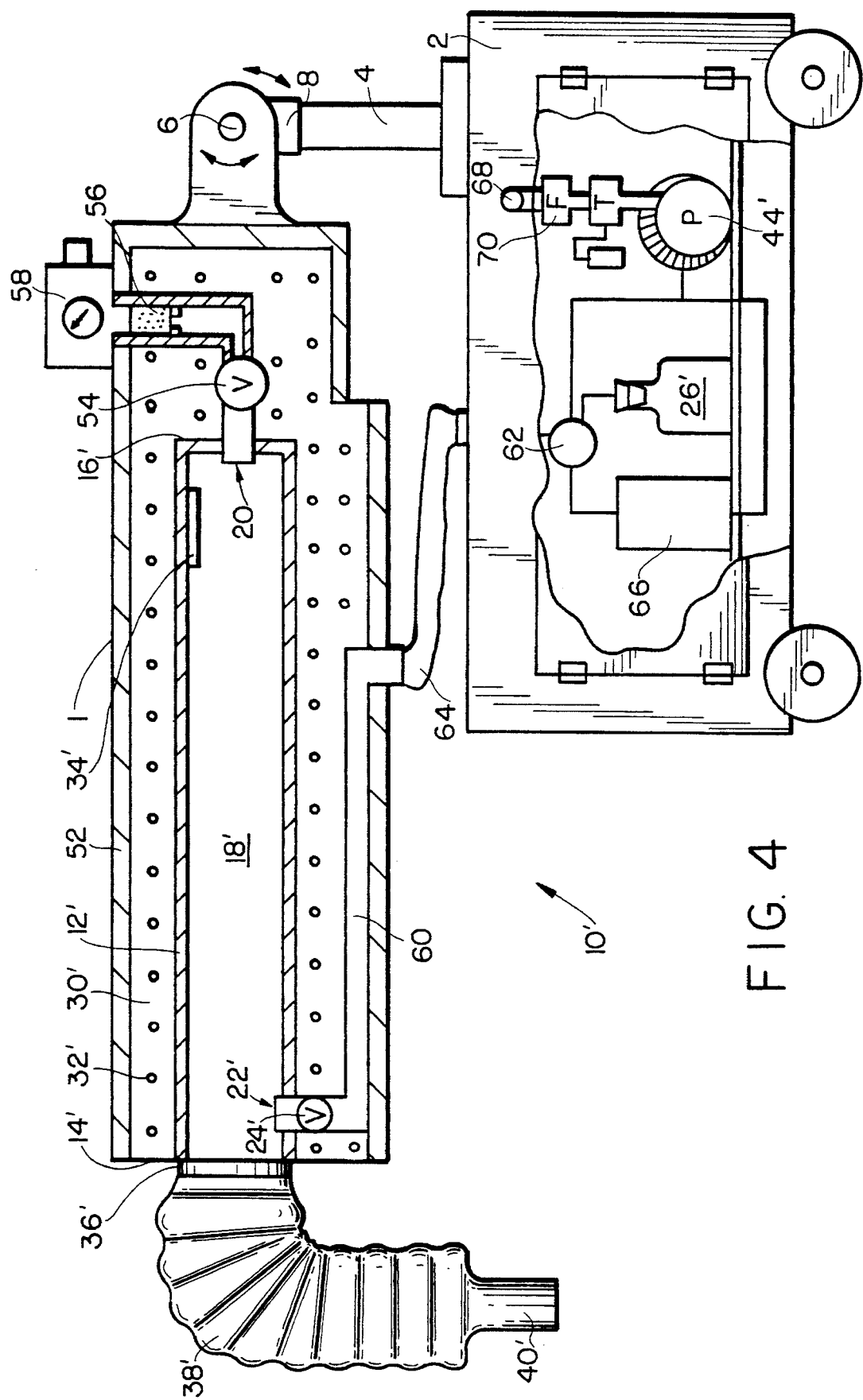
FIG. 4 is a cross-sectional view in-part of the embodiment apparatus shown schematically in FIG. 3, with some component parts exaggerated in size (not to scale).

It will be appreciated that when the apparatus of the invention is to include processing components as described above, it may require bulky and cumbersome additional equipment which obviates the hand-held, hand-operated features of the apparatus 10. However, the basic components of the apparatus 10 can still be employed with slight modification to have a portable, relatively compact apparatus 10. Referring to FIG. 3, there is seen a block diagram showing the essential components of a preferred embodiment portable apparatus of the invention. FIG. 4 shows in further detail the embodiment apparatus 10' of the invention where components as described above in relation to the apparatus 10 have same numerical designations, with the addition of a prime symbol.

FIG. 4 is a cross-sectional (in-part) side view (not to scale and with parts exaggerated in size) of an embodiment portable apparatus 10' of the invention. The apparatus 10' shown includes a movable arm 1 mounted on a wheeled truck 2 through stanchion 4. The arm is movable in a vertical ARC (as shown by the double-headed arrow) by pivoting on pin 6 and along a horizontal plane (as shown by the double headed arrow) on swivel joint 8. The arm 1 comprises a housing 52 for enclosing a breath reservoir container 12' identical to container 12 previously described. Aside from the features relating to hand grips, the apparatus 10' differs from the apparatus 10 in respect to the following. Flap valve 28 has been replaced with a solenoid actuated valve 54. The vent 20 includes a microorganism filter 56 and a respirometer 58. The outlet of portal 22 has been extended through conduit 60 within the heating sleeve 30' and is connected to the interior of truck 2. The vessel 26' is housed in truck 2 and receives collected breath when selected through the 3-way tap 62 connected to conduit 60 via a flexible hose 64. The tap 62 is connected also to trap 66 for adsorbent, chemical or cryogenic trapping as previously described. Vacuum to trap 66 or vessel 26' is provided by the vacuum pump 44'. The pump vents through vent 68, after passage through a microorganism filter 70.

The embodiment apparatus 10' is operated in a similar manner as the apparatus 10. When an adsorbent trap such as trap 66 is to be activated for processing, the procedure is advantageously as follows:

(1) The subject either sits or stands comfortably while breathing normally into the mouthpiece 40'. After one minute (to fill the reservoir, and accustom the subject to the apparatus), the pump 44' is started with the tap 62 set to bypass to flush the apparatus 10' with alveolar breath. The subject inspires untreated room air.

(2) After one minute of bypass, the tap 62 is adjusted so that alveolar breath passes through the adsorbent trap 66. In practice, a usable sample (10 1) may be collected using a flow rate of 2.0 l/min for 5.0 minutes. However, smaller or larger samples may be collected as desired.

(3) At the conclusion of the collection, the trap 66 is withdrawn from the apparatus and enclosed in a hermetically sealed container for transport to an analytical laboratory.

(4) The process is then repeated (or was performed beforehand) except with disconnection from the patient in order to collect a sample of the inspired (room) air for a control sample. In all operations of the apparatus 10 or 10', a control sample of inspired (room) air is collected either immediately before or after the breath sample and analyzed in the same fashion. The volatile organic compounds in this sample are then subtracted from the volatile organic compounds in the alveolar breath in order to accurately determine the breath signal.

(5) The samples are then taken to the laboratory for analysis by standard laboratory methods.

The method of the invention has been used without patients experiencing any adverse effects the results may be summarized as follows.

(1) Normal subjects: Approximately 40–80 volatile organic compounds are routinely observed in most samples; these have been tentatively identified by GC/MS. More than 100 different compounds have been observed altogether (not everyone has the same compounds in their alveolar breath).

(2) Patients with schizophrenia: Abnormal levels of two compounds (pentan and carbon disulfide) have been observed. In addition, using special computer software for pattern recognition analysis, breath analysis identified patients with schizophrenia with a sensitivity of 68% and a specificity of 84%.

(3) Environmental toxicology: using the subtraction methodology described above, it has been possible to determine which of the volatile organic compounds observed in human breath are derived from breathing polluted air. Volatile organic compounds implicated in the etiology of coronary heart disease (carbon disulfide) and liver cancer (tetrachloroethane) have been observed in the breath of normal subjects living in New York City, N.Y.

(4) In-vitro studies of cancer cells: the method has been used to collect head-space air samples from in-vitro preparations of cancer cells. Preliminary data indicate that lung cancer cells manufactured compounds in-vitro which are not seen in non-cancerous cells derived from the lung, suggesting that breath volatile organic compounds might be of value for the early diagnosis of lung cancer.

(5) In-vitro studies of bacteria: the method has been used to collect head-space air samples from in-vitro preparations of bacteria (Staphylococci, Streptococci, and Pseudomonas). All yielded different patterns of volatile organic compounds, suggesting that breath might be of value in diagnosing the bacterium in patients with pneumonia.

Those skilled in the art will appreciate that many modifications of the above-described preferred embodiments may be made without departing from the spirit and the scope of the invention. For example, a microprocessor may be employed to sequence the events (opening and closing valves; controlling temperature). As another embodiment apparatus of the invention, reference is made to the schematic FIG. 5, wherein there is shown a breath collection device 200 assembled from the following parts, identified by the numerals:

202. Mouthpiece (disposable)
203. Flap-valve assembly (disposable)
204. Temperature sensor probe
205. Temperature controller. Input from C provides information to
206. switch power output to 208 on or off
207. Stainless steel tube (flexible). An exit portal of the tube is open to the atmosphere. The first part of this resides in a swinging arm; the second part is in a box
208. Heating jacket (maintains 207 at 40 deg C.)
209. Three-way tap, switched by solenoid
210. Bypass line
211. Stainless steel container for 213
212. Screw-top for 211 sealed with O-ring
213. Trap (stainless steel tube containing adsorbent material)
214. Flow rate controller (needle valve with knob)
215. Flow meter (rotameter or mass flow detector)
216. Pump (vents to atmosphere)
217. Timer control (controls solenoid switch on 209 and pump 215) (may have digital display on which collection time is entered and displayed).

Figure 5:
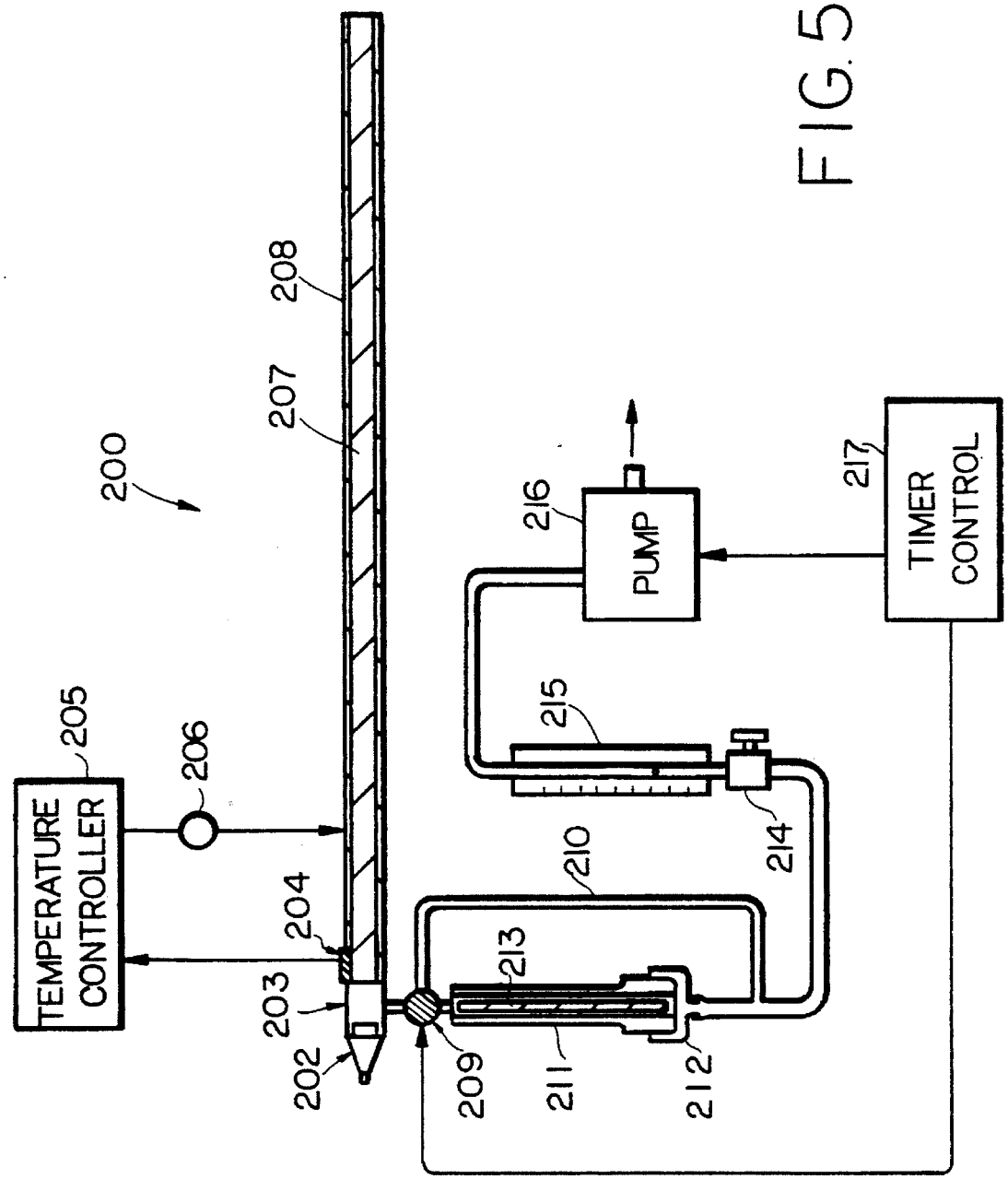
FIG. 5 is a schematic diagram of another embodiment apparatus of the invention.

The apparatus 200 of FIG. 5 is operated in the same manner as the device 10 described above.

I claim:

1. Apparatus for the collection of alveolar breath from a mammal for analysis, which comprises;

A. a fluid reservoir tubular container having
      (a) a first end;
      (b) a second end;
      (c) a container body extending from the first end to the second end, and which with the first and second ends defines an interior chamber with a capacity of about 3 liters, said body being of a tubular configuration whereby breath introduced into the first end will travel to the second end when the second end is vented;
      (d) a breath entry portal in the body, proximal to the first end distal, to the second end;
      (e) a breath exit portal in the body, proximal to the second end and distal to the first end and open to the atmosphere; and
      (f) a sampling portal in the body of the reservoir container, at a point between the entry and the exit portals;

B. means for maintaining said chamber at a temperature sufficient to prevent condensation of water and volatile compounds in the mammal's breath, associated with the reservoir container;

C. means for sealed coupling of the reservoir container entry portal to the pulmonary airway of the mammal, whereby exhaled breath is directly delivered at full, undiluted concentration of compounds contained in the breath, to the reservoir container;

D. a sample container means for holding samples of the breath exhaled by the mammal into the reservoir container and selected for analysis to determine quantitative presence of those compounds of interest;

E. valve means between the sampling portal of the reservoir container means and the sample container for selectively directing breath samples from the reservoir container to the sample container;

F. means for maintaining the selected breath at a temperature sufficient to prevent water condensation in the sample contained and the valve means for directing samples to the sample containers means; and G. pump means for moving selected samples of the breath from the reservoir's container into the sample container means.

2. The apparatus of claim 1 wherein the sampling portal is proximal to the breath entry portal and distal to the breath exit portal.

3. The apparatus of claim 1 wherein the means for maintaining the chamber at a temperature sufficient to prevent condensation comprises a resistance heater enclosed in a sleeve surrounding the container body.

4. The apparatus of claim 1 wherein the means for sealed coupling comprises a wide bore tube connected at one end to the breath entry portal and at the other end to a mouthpiece for sealed fitting with the oral lips of a mammalian subject.

5. The apparatus of claim 1 wherein the pump means comprises a syringe pump.

6. The apparatus of claim 1 wherein a thin-film thermistor within the chamber controls the means for maintaining the temperature.

7. Apparatus for the collection of alveolar breath from a mammal, which comprises;

(A) a movable arm mounted on the exterior of a (B) housing, said arm carrying
  (i) a tubular reservoir container having a first end, a second end and a body extending between the first and second ends, said body defining an interior chamber; and a sampling portal in the body of the container;
  (ii) means for maintaining the temperature of the chamber at about 40° C.;
  (iii) means for connecting the pulmonary airway of a mammal to the chamber;
  (iv) valve means for controlled venting of the chamber; and
  (v) conduit means connecting the sampling portal to a breath collection vessel means described hereinafter;
(B) said housing (B) enclosing:
  (i) said vessel means, connected to the conduit means, for holding samples of breath selected from the reservoir container through the sampling portal; and
  (ii) means for maintaining the temperature of said vessel means at about 40° C.

8. The apparatus of claim 7 wherein the housing also enclosing pump means for moving breath samples through the conduit means into the vessel means.

9. Apparatus for the collection of alveolar breath from a mammal, which comprises;

(A) a movable arm mounted on the exterior of
(B) a housing, said arm carrying
  (i) a tubular reservoir container having a first, and a second end and a body extending between the first and second ends, said body defining an interior chamber; and a sampling portal in the body of the container;
  (ii) means for maintaining the temperature of the chamber at about 40° C.;
  (iii) means for connecting the pulmonary airway of a mammal to the chamber;
  (iv) valve means for controlled venting of the chamber; and
  (v) conduit means connecting the sampling portal to a breath collection vessel means described hereinafter; said housing enclosing:
(B) (i) vessel means connected to the conduit means, for holding samples of breath selected from the reservoir container through the sampling portal;
  (ii) means for maintaining the temperature of said vessel at or about 40° C.
  (iii) pump means for moving breath samples through the conduit means into the vessel means; and
  (iv) a valve means actuable to direct the moving breath sample to a trap connected to the pump or to the vessel.

10. The apparatus of claim 9 wherein the trap is selected from the group consisting of an adsorptive trap, a cryogenic trap or a chemical trap.

11. The apparatus of claim 10 which further comprises a vent on the valve means for controlled venting.

12. The apparatus of claim 11 wherein the pump means exhausts through the vent.

* * * * *